US011026776B1

(12) United States Patent  
Raju

(10) Patent No.: US 11,026,776 B1  
(45) Date of Patent: Jun. 8, 2021

(54) OPTIMAL SIZING OF ILIAC VEIN STENTS AND METHOD OF USING

(71) Applicant: Seshadri Raju, Jackson, MS (US)

(72) Inventor: Seshadri Raju, Jackson, MS (US)

( * ) Notice: Subject to any disclaimer, the term of this patent is extended or adjusted under 35 U.S.C. 154(b) by 0 days.

(21) Appl. No.: 16/438,068

(22) Filed: Jun. 11, 2019

Related U.S. Application Data

(63) Continuation-in-part of application No. 14/665,602, filed on Mar. 23, 2015, now abandoned.

(60) Provisional application No. 62/742,732, filed on Oct. 8, 2018, provisional application No. 62/745,667, filed on Oct. 15, 2018.

(51) Int. Cl.
| | |
|---|---|
| *A61F 2/06* | (2013.01) |
| *A61B 8/06* | (2006.01) |
| *A61B 8/08* | (2006.01) |
| *A61B 5/107* | (2006.01) |
| *A61B 8/12* | (2006.01) |

(52) U.S. Cl.
CPC .................. *A61F 2/06* (2013.01); *A61B 8/06* (2013.01); *A61B 8/0891* (2013.01); *A61B 5/107* (2013.01); *A61B 8/12* (2013.01)

(58) Field of Classification Search
None
See application file for complete search history.

(56) References Cited

U.S. PATENT DOCUMENTS

| | | | |
|---|---|---|---|
| 2003/0171894 A1* | 9/2003 | Giovanni Battista Mancini | ......... G06F 19/324 702/182 |
| 2015/0173716 A1* | 6/2015 | Lee | .......................... A61B 8/06 600/441 |

\* cited by examiner

*Primary Examiner* — Oommen Jacob  
*Assistant Examiner* — Shahdeep Mohammed  
(74) *Attorney, Agent, or Firm* — Intellectual Property Consulting, LLC; Bernard F. Meroney

(57) ABSTRACT

Whether a vein has a stenosis may be determined using duplex ultrasound (DUS). A method of diagnosing stenosis includes: identifying a patient exhibiting at least one of a group of symptoms in at least one limb consisting of: pain, discomfort, swelling and venous stasis skin changes including ulceration; using duplex ultrasound to measure a cross-sectional area of a vein; and, if the cross-sectional area is less than or equal to 50% of a predetermined anatomical minimum for the vein, diagnosing the vein as stenotic. A device for diagnosing stenosis may include: a duplex ultrasound; a display; and a processor configured to show on the display a cross-sectional area measurement of a vein. Stenosis may be treated by inserting a stent in the vein. The predetermined anatomical minimum for the vein is a predetermined calculated valve based on physical principles. It is not a measured value from the patient, or any patient, or a population of patients.

6 Claims, 15 Drawing Sheets

DUS/Ivus CIV

OPTIMAL SIZING OF ILIAC VEIN STENTS AND METHOD OF USING

Cross Reference to Related Applications

This application is a continuation-in-part of U.S. Application No. 14/665,602, filed on Mar. 23, 2015; and this application claims priority to U.S. Provisional Application No. 62/742,732, filed on Oct. 8, 2018; and this application claims priority to U.S. Provisional Application No. 62/745,667, filed on Oct. 15, 2018, and the contents of those applications are hereby incorporated by reference.

BACKGROUND

Vein obstruction, particularly iliac vein obstruction, is a major component of chronic venous disease (CVD). Vein stenting is increasingly used after more conservative therapy has failed. Stenting has an attractive therapeutic profile with good long-term patency, safety, and efficacy. The therapeutic effect is primarily due to relief of venous hypertension. In the iliac vein, there is decompression of the peripheral venous tree following iliac vein stenting, with significant reduction of foot venous pressure.

Vein stents should be of a size that provides outflow with low resistance to normalize elevated venous pressure in the limb. However, there is no consensus of "optimum" outflow/stent size. Peripheral venous pressure is controlled by a set of central and peripheral factors. The most important peripheral variable is vein caliber as conductance/resistance (hence pressure) is related to the fourth power of radius. Caliber of the iliac-femoral outflow is a key variable in the control of peripheral venous pressure because it is correctible while other variables, such as compliance or inflow, are not. The purpose of stent correction is to restore the lumen area to an optimal value that would provide maximal decongestion of the peripheral venous bed and lower peripheral venous pressure. The optimal outflow caliber should preferably match rate of inflow to maintain stable peripheral venous pressure.

We have analyzed the "optimum" size stents for the main vein segments, using a variety of techniques. These optimum sizes represent the minimum stent size to be deployed in an adult, and the stent sizes are not dependent on the measurement type used (e.g. IVUS, DUS, any other measurement type) to determine that a stent is desired. Instead, the stent sizes to be used only depend on the location of the stenosis, in the EIV, CIV, or CFV. These optimal sizes are then utilized in a procedure to determine if a stent is needed, and if needed, the stent size to use.

BRIEF DESCRIPTION OF THE DRAWINGS

For a further understanding of selected methodologies, reference should be made to the following description taken in conjunction with the accompanying drawings in which like parts are given like reference numerals.

DETAILED DESCRIPTION OF THE INVENTION

Techniques for Determining Minimal Stent Sizes

The first technique attempted was to determine optimal vein stent size by measuring the caliber of iliac-femoral vein segments in a set of normal healthy volunteers. Initially, supine foot venous pressure and diameters of the iliac-femoral vein segments were measured by Duplex ultrasound (DUS) in 10 normal healthy volunteers without a history or clinical signs of CVD. This was an effort to establish "normal" caliber of these veins. This approach initially failed, as many of the "normal" volunteers were found to have silent iliac vein stenosis, as is known to occur, thereby altering the size distribution. Instead, the patient set was changed to encompass a large subset of patients, each displaying some symptoms of CVD. Vein parameters were determined by IVUS. The lumen area was derived from IVUS planimetry of CIV, EIV, and common femoral vein (CFV) in a large subset of patients (n=345).

Figure 14A:
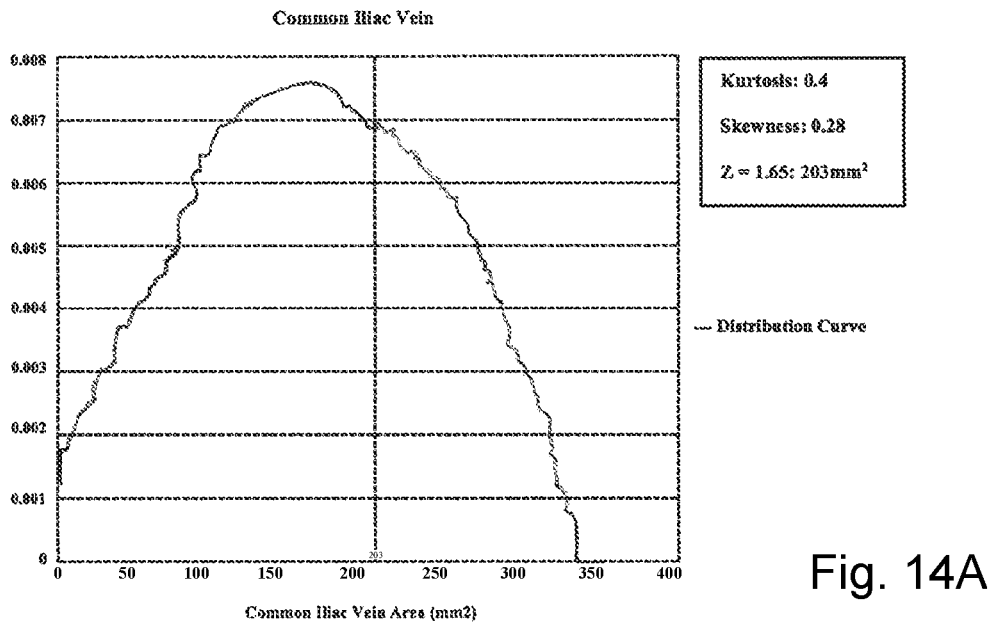
FIG. 14A is a distribution of measured lumen area sizes in the common iliac vein in a population with characteristics of CVD.
Figure 14B:
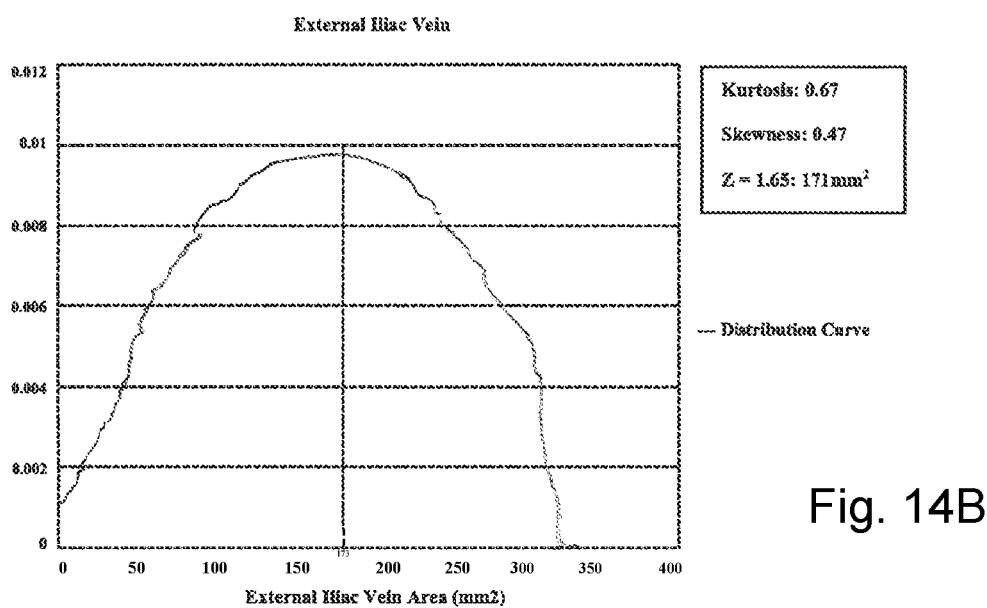
FIG. 14B is a distribution of measured lumen area sizes in the external iliac vein in a population with characteristics of CVD.

The CIV is about 2 cm in size on gross inspection during open vascular procedures. The EIV and CFV are a few mm smaller. The three vein segments (CIV, EIV, and CFV) frequently measure 16, 14, and 12 mm respectively on IVUS examination of segments free of disease. The distribution curve for the iliac veins measured is shown in FIG. 14. The lumen area distribution curves of iliac femoral vein segments display a wide range (FIG. 14(a) and (b)). The data points at the extreme (5%) right tail of the curve, a (Z-score of >1.65), should approach normal (nonstenotic values) per distribution theory. Respective Z line intersection (>1.65) values for the vein segments are shown in Table 1. "Normal" lumens of the various segments are expected to be circular or nearly so with normal hydration." The lumen diameters shown in Table 1 for the CIV and the EIV are derived values from the area, and are tentatively identified as "optimum." However, given the inherent potential errors in his procedure's assumptions (an assumption that the distribution of diseased lumen's size are normal distributions, and an assumption that the sample size is sufficiently large enough) these values are used only as a check for the reasonableness of the remaining calculated methods.

The second technique used was to predict "optimal" stent size using the hydrodynamic relationships, including the expression between flow, pressure and resistance, (Flow Q=ΔP/R)

and the Poiseuille equation, $$\Delta P = \frac{8\mu L Q}{\pi r^4}$$

The arterial inflow into both the lower limbs and pelvis (and by inference, outflow through common iliac vein (CIV)) and fluid flow rates is 1500 mL/s in normal individuals at rest. This represents a constant fraction (~21%) of cardiac index. Each common iliac outflow "Q" is 750 mL/s, occurring mostly in expiration. Using the normal inspiratory/expiratory ratio of 1:2 the value of Q in the equations is 19 mL/s. The value for L is 4 cm (length of the CIV) and μ is 0.04 Poise. With these inputs, the pressure gradient offered by a given caliber stent can be calculated from the Poiseuille equation. As an example, resistance, in dynes/cm² for a 10 mm diameter stent (0.5 cm radius), will be in in normal flow ---

$Fx=0.4P*4L/[0.54*\pi*(0.5^4)]$ yielding a resistance value of 124 dynes/cm² . Normally, there is little measurable gradient in the abdominal veins during phasic periods of flow. An optimum size for the stent should yield a negligible gradient with margin to spare to account for increased flow with exercise (~3 times) and for in-stent restenosis (ISR) that often occurs after stent placement. The estimates derived from Poiseuille law are derived fusing generic inflow data. More precise individualized estimates may be possible if common iliac arterial flow can be determined with accuracy. Noninvasive technology to do this is not yet available.

The pressure gradient in stents of different caliber is shown in Table 2. Values are shown for flow at rest, during exercise (3×resting flow) and when the stent is involved in 50% diameter stenosis due to ISR/compression. The optimal size of the stent for the CIV appears to be ~18 mm.

The third technique used was to predict stent size with Young's scaling rule. It has been known that parent to daughter branches in the vascular system had a diameter ratio of 1.26:1 (or a daughter to parent ratio of 0.79:1) that held constant across several generations of vascular branching. This scaling rule is generally attributed to Thomas Young, but probably predated him.[6] This is a fundamental law of efficient branching to maximize flow with the least expenditure of energy. The scaling proportion tends to optimize several key flow parameters such as flow volume, velocity, resistance/conductance, and Reynolds number. The relative caliber of iliac vein segments can be projected using the scaling rule from femoral vein caliber, which is well known. The projections yield the upper limit of upscaling required of the parent vein, as confluence of equal caliber daughter veins is assumed. The external iliac vein (EIV) and CIV are both born of the confluence of large and smaller tributaries (CFV and saphenous; EIV and hypogastric) and diameters can also be estimated using Young's relationship.

The projected CFV diameter from the scaling law closely corresponds to actual measured femoral vein diameter (mean 11.8 mm) recorded by Fronek in a large (n=3539 limbs) population study; the estimated "normal" caliber of the three iliac-femoral vein seg-ments derived from the various methodologies described above are closely similar as shown in Table 3. Table 4 shows our recommendation of the optimal minimum size of stents to be used for the various segments. This is also the target size in re-interventions to correct ISR/stent compression. Diameters of EIV and CFV (two generations) can be projected from the CIV diameter estimated by the above two methods (Young's scaling and Poiseuille law). The projected CFV diameter derived from the scaling law closely corresponds to actual measured femoral vein diameters (mean 11.8 mm) recorded by Fronek in a large (n=3539 limbs) population study. The estimated "normal" caliber of the three iliac-femoral vein segments derived from the various methodologies described above are similar as shown in Table 3.

Table 4 shows the recommended minimum size of stents to be used for the various segments. It is preferred that these be minimal diameters, and more preferred, that slightly larger diameter stents (such as 2 mm larger) be used to account for re-interventions. These are also the target size, in re-interventions, to correct ISR/stent compression, based on Young's scaling and Poiseuille's law.

Procedure for Determining Stenosis and Stent Size

Practical Considerations

When determining stenosis, grading the severity of stenosis should be based on this optimal caliber, rather than adjacent or contralateral lumen as comparators as iliac venous outflow has an "optimal" caliber. Otherwise, in situ measurements of "normal" may result in underestimation of the stenosis, particularly when long diffuse lesions present. Elevated peripheral venous pressure from causes other than outflow stenosis (e.g. congestive failure, A-V fistula) will have a normal outflow caliber on IVUS examination.

Stent function is open to decay by development of in-stent restenosis (ISR). Up to 25% reduction in flow channel diameter is common in ISR. Stent compression from outside by development of recurrent stenosis in the native vein also occurs. Typically oversize stents are (oversized by 2 mm beyond recommended caliber) deployed, but post dilatation is restricted to the optimum outflow caliber for the segment. This over-sizing allows for later aggressive dilatation during re-interventional correction when necessary. The "normal" caliber of the iliac outflow tract is not easily determinable by direct measurement. A variety of indirect methods have been used to arrive at an estimation, as described above. The optimal recommended stent caliber is the target used to restore diseased lumen during initial stent placement (and also at re-interventions), plus 2 mm. The predicted optimum lumen diameter or optimal lumen area should also be used when determining if intervention, such as stent placement, is desired. For instance, the following methods may be employed.

Stenosis is a narrowing or partial occlusion of a lumen, such as in the arterial or venous system and is usually characterized by a rapid change in lumen cross-sectional area that occurs over a very short segment length of the vessel, typically over a length of about 1 to 2 cm (a focal stenosis). A diffuse stenosis is stenosis that is not focal, and is characterized by a narrowing of the lumen which occurs over greater vessel segment length, typically lengths greater than 2 cm. Stenosis is accompanied by changes in velocity of blood flow through the narrowed lumen. Abnormally high local velocity changes in a vein are those associated with stenosis. Specifically, blood flow through a stenosis can result in an increase in velocity through the narrowed section. Consequently, stenosis is often identified based on changes in fluid velocity, such as detected by duplex ultrasound devices (DUS).

The minimal anatomical mean cross-sectional areas for veins segments, that is, the optimal area (for adults in a supine position), discussed above, above, and the associated closest integer diameter for a circular lumen, are as follows:

| | Area | approximate integer diameter (for stents) |
|---|---|---|
| Common iliac vein (CIV) | 200-250 mm$^2$ | 16-18 mm |
| External iliac vein (EIV) | 150 mm$^2$ | 14 mm-15 mm |
| Common femoral vein (CFV) | 110 mm$^2$ (DUS; 125 mm$^2$ (IVUS ) | 12 mm |

Note, for the common femoral vein, the DUS determined area should be 110 mm$^2$, while the IVUS measurement used for comparison purposes is 125 mm$^{2t}$ DUS generally understates measurements of area or diameters, as opposed to IVUS, and this is more apparent with smaller lumens, such as the CFV. If CFV lumen measurement is made with IVUS, the area measured should be compared with 125 mm $^2$. If the CFV lumen measurement is made with DUS, the measured area should be compared with 110 mm $^2$ to compensate for the tool.

Direct measurement of vessel cross-sectional area can be made with intravascular ultrasound ("IVUS"). However, the IVUS procedure is an invasive procedure, where the sensor ultrasonic probe is inserted into the lumen. It would be advantageous to be able to determine lumen cross-sectional area using a non-invasive procedure. However, the above minimums can also be used to detect stenosis if IVUS is used directly.

Intravascular ultrasound (IVUS) is the gold standard to assess vein stenosis, particularly iliac vein stenosis. External duplex ultrasound (DUS) measurements may be employed to help determine cross-sectional area, and using the disclosed method can achieve results similar to IVUS to determine the absence or presence of stenosis. DUS-determined "stenosis" conditions that are sufficiently significant should be confirmed using IVUS and/or Magnetic Resonance Venography (MRV). The use of DUS area measurements to determine the degree of vessel stenosis varies from traditional duplex methodology, which instead relies on visual identification of focal stenosis and measured local velocity changes.

Arterial stenosis predates knowledge and measurement of venous stenosis. The criteria for diagnosing arterial stenosis is based on lumen narrowing. Generally, it has been demonstrated that forward flow to a limb or organ supplied by the artery drops off significantly when the stenosis reaches above 70% compared to the immediately adjacent lumen where no narrowing is apparent. This significant stenosis indicator has been unadvisedly applied to venous stenosis. The clinical effects of chronic venous disease are based on venous back pressure (on the lower limb veins), not diminished forward flow, as in arteries. Thus the arterial criterion of severe stenosis, based on comparison to a base lumen size adjacent to the stenosis, is not predictive for instances of diffuse stenosis. Serious venous back pressure may result from stenosis much smaller than 70% stenosis.

Because peripheral venous pressure is substantially the same physiologically in healthy individuals, (at about 11 mm Hg), it makes sense that lumen area reduction in main venous conduits will elevate back pressure or peripheral venous pressure. As discussed above, Anatomic lumen diameter and cross-sectional area appear to be fairly consistent in healthy individuals, and consequently, a determination of cross-sectional area can be used to diagnose stenosis. The only direct cross-sectional area measurement currently available is using invasive IVUS.

A cross-sectional area may be estimated using non-invasive DUS procedures, and predictions made based on the DUS measurements. While not as exacting as an IVUS measurement, DUS measurements, have very few false negatives. Hence, if a DUS determined measurement is negative, IVUS is not necessary to confirm the lack of stenosis, and the physician can proceed to investigate another basis of the patient's symptoms. Contrarily if DUS based cross-sectional measurements are positive for area stenosis, then IVUS is indicated to verify the stenosis, and significant stenosis will be found in a large percentage of such cases.

Figure 1:
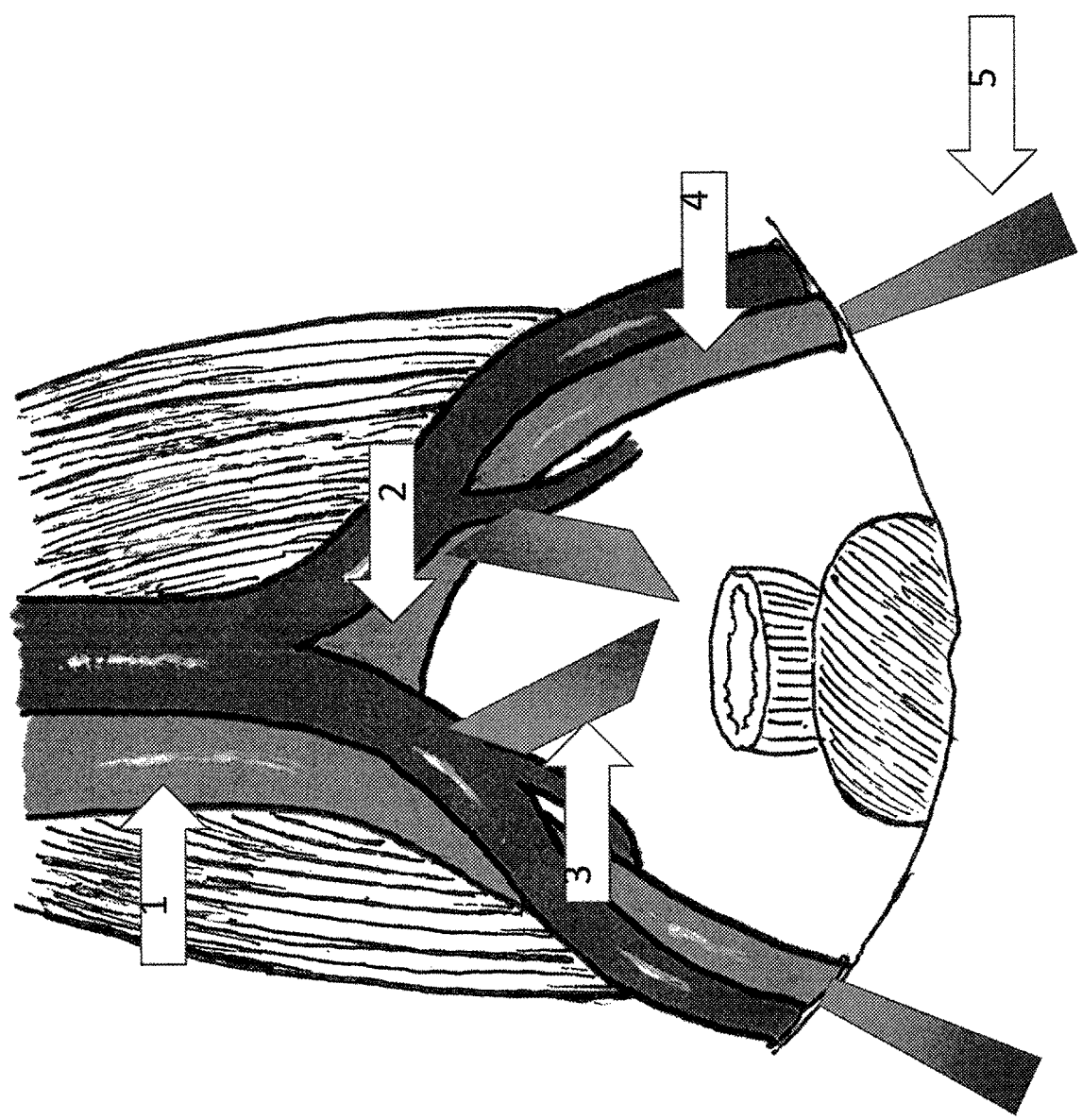
FIG. 1 is a drawing showing the veins in a portion of a human pelvis.

FIG. 1 shows portions of a human pelvis. The inferior vena cava (IVC) 1 is in communication with the common iliac vein (CIV) 2, the internal iliac vein (IIV) 3, the external iliac vein (EIV) 4, and the femoral vein (FV) 5. The FV 5 becomes the EIV 4 after crossing the inguinal ligament, which is shown as a U-shaped line. The EIV 4 becomes the CIV 2 after it joins the IIV 3. The right and left CIVs 2 (only one labeled) join together to form the IVC 1.

There are some anatomic differences between the right and left veins. The left iliac veins is more curvaceous while on the right side, it is straighter in frontal projections. But both veins curve (less on the right) in the sagittal plane, which is primarily visible in lateral views. Note the left hypogastric artery (unlabeled) crosses the EIV 4, but the right hypogastric artery does not.

Figure 3:
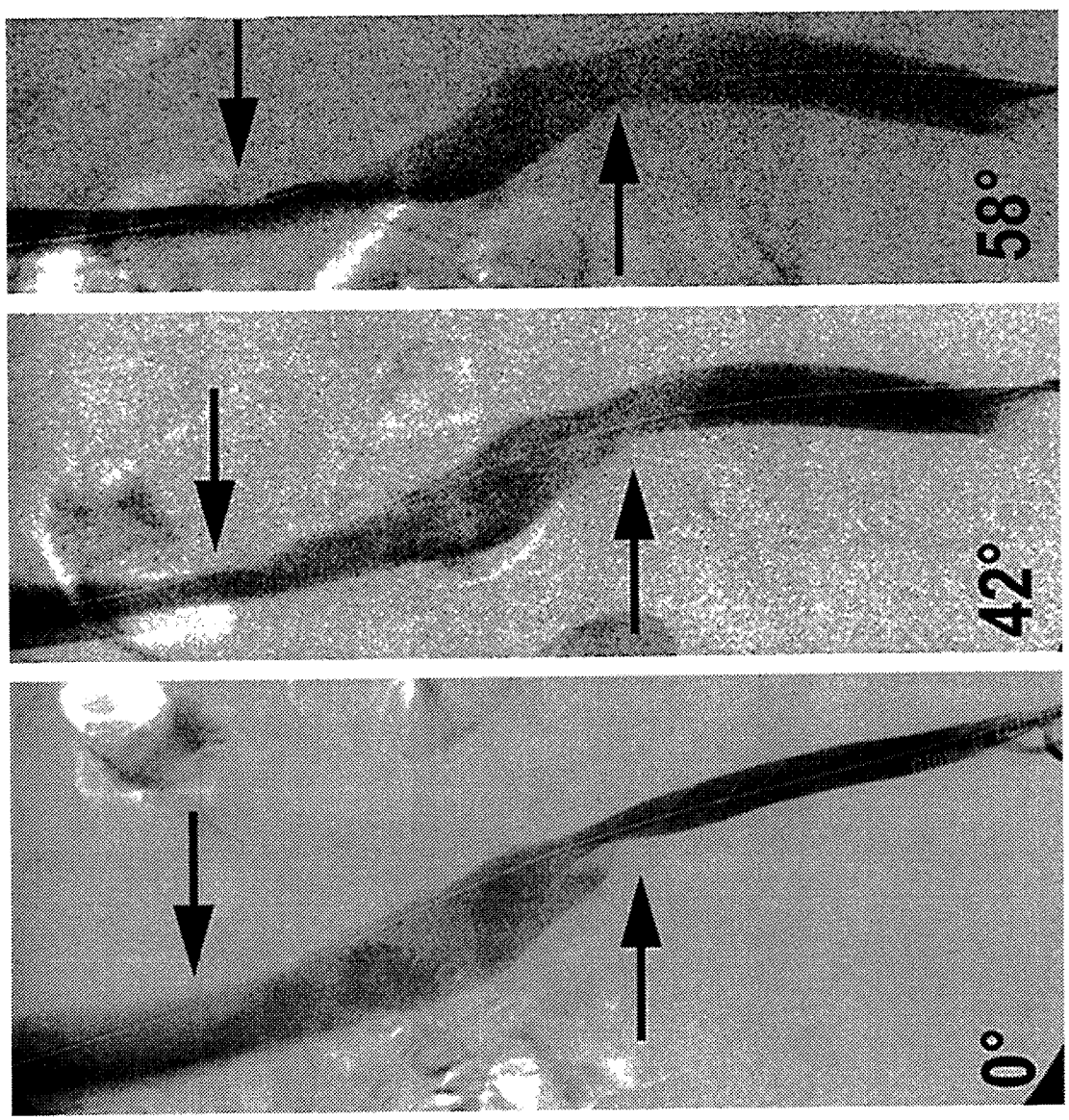
FIG. 3 are x-ray angiogram biplane projections of an adult human pelvic veins with frontal (0°), 42°, and 58° views.

FIG. 3 shows an EIV, with the IIV viewable as a short stump in the frontal)(0° view. Note the greater curve in the lateral projection at 58%. The upper and lower arrows show stenotic lesions that are visible in one projection but not the other, meaning some lesions are not three-dimensional, but two-dimensional. In other words, the veins may be compressed from front-to-back or side-to-side, and not necessarily circumferentially. These images indicate that the measured diameter of the vein may differ significantly based on the angle of view. However, with DUS measurement, the angle of view is essentially constant-near perpendicular to the exterior of the body). DUS measurements may have some degree of angularity built in based on the type of beam output by the transducer (e.g., linear, sector and curved). Additionally the transducer may be manually tilted to vary the 'angle of incidence (the angle at which the Doppler beam strikes the interrogated vein).

Figures 4A, 4B, 4C:
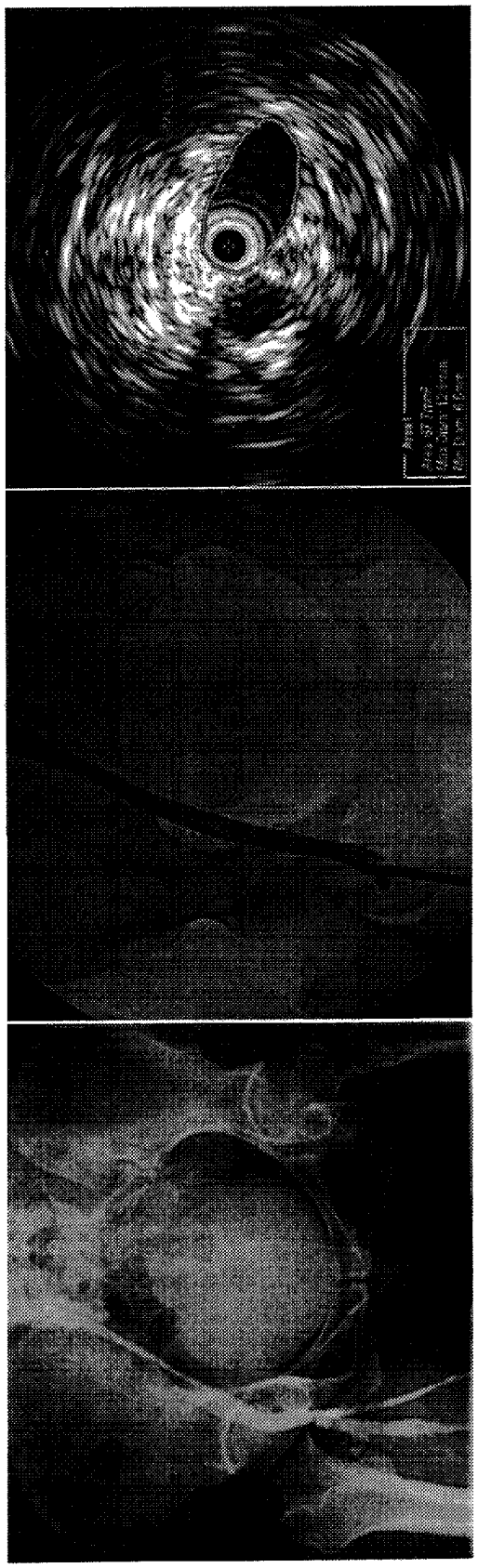
FIG. 4A and 4B are x-ray angiogram images of a human pelvis.
FIG. 4C is an intravascular ultrasound image of the iliac veins depicted in 4B.

FIG. 4 shows classic diffuse type stenosis. The constricted lumen of the iliac vein is unmistakable in FIG. 4C. Nonetheless, venographic appearance may be 'normal' in other cases, as shown in FIG. 4B on IVUS examination, shown in FIG. 4C, the iliac veins in this patient was diffusely narrow, measuring only about 12.8 x 6.5 mm in its greatest and least diameters. The elliptical shape probably explains "normal" venographic appearance in frontal projections. The lumen area of the CIV in non-diseased normal patients is approximately 200 mm$^2$. The lesion in this patient measured 67 mm$^2$, representing a 66% stenosis.

Figure 5B:
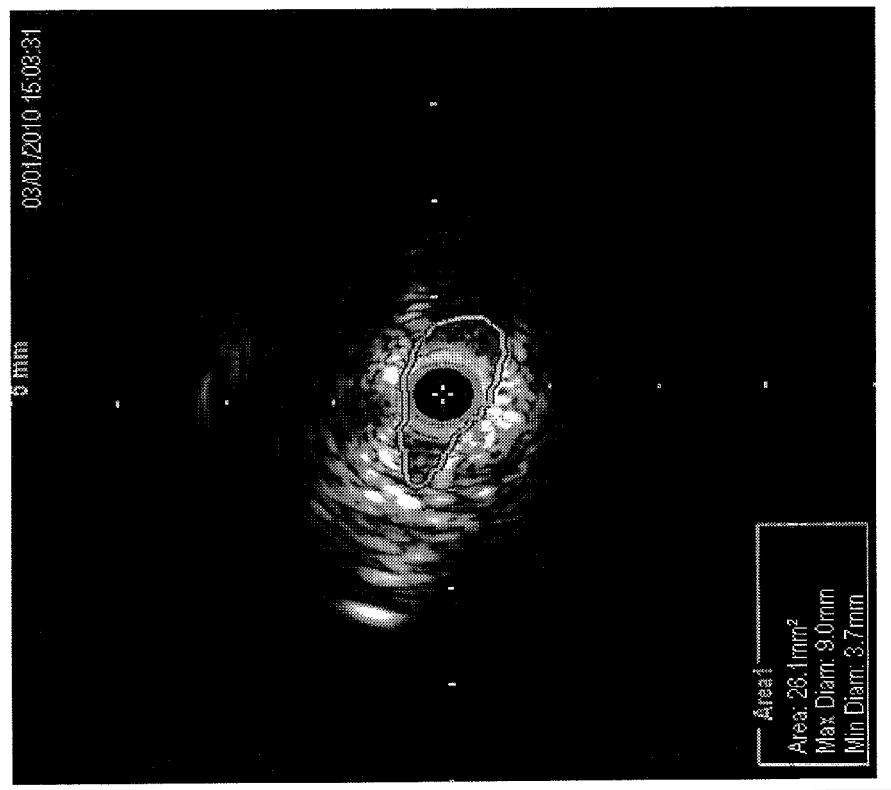
FIG. 5B is an intravascular ultrasound image of the vein shown in FIG. 5A indicating diffuse, Rokitanski-type stenosis.
Figure 5A:
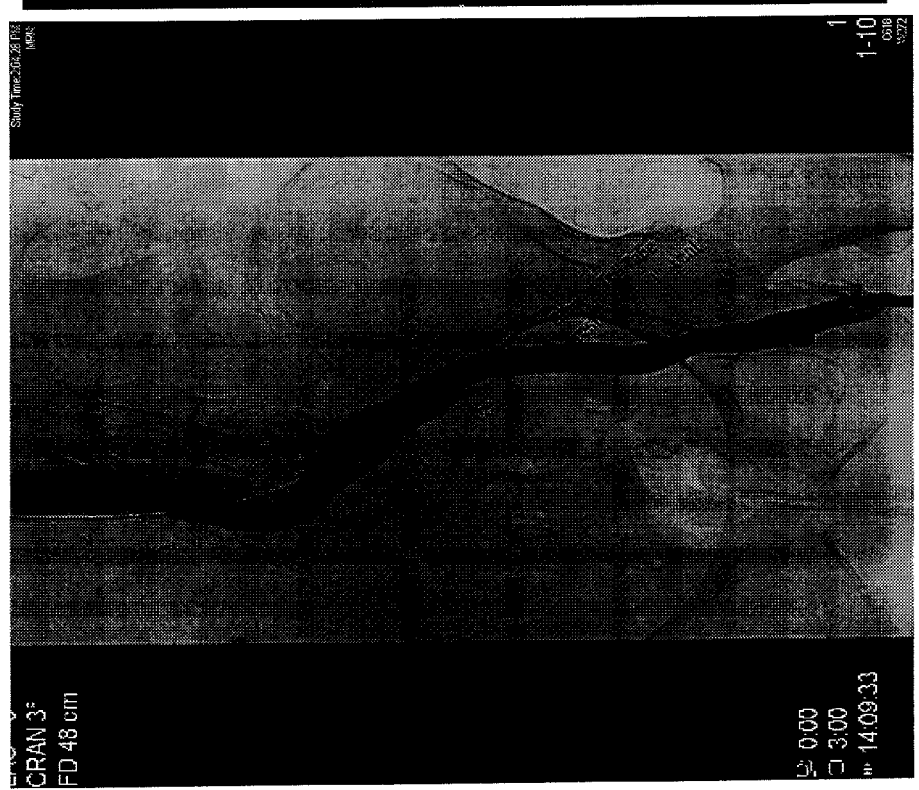
FIG. 5A is an x-ray angiogram image of a common iliac vein with no focal narrowing or stenosis visible.
Figure 6A:
FIG. 6A is a x-ray angiogram image of a common iliac vein with no focal narrowing visible.
Figure 6B:
FIG. 6B is an intravascular ultrasound image of the vein shown in FIG. 6A indicating diffuse, Rokitanski-type stenosis.

FIGS. 5A-5B and 6A-6B are additional examples of how the area method of this disclosure may find stenosis missed by venography when diffuse stenosis is present. Venographic images FIG. 5A and 6A show no focal stenosis in a CIV vein segment, i.e., no focal narrowing is visible. However, the corresponding intravascular ultrasound images 5B and 6B indicate diffuse-type stenosis. FIGS. 5B and 6B show cross-sectional areas of 26 mm$^2$ (about 75% stenosis) [(1.0-{measured area/predetermined area})*100] and 97 mm$^2$ (about 50% stenosis), respectively, i.e., about less than or equal to 50% of the anatomical predetermined mean cross-sectional area for a CIV vein segment.

Figure 7B:
FIG. 7B is an intravascular ultrasound image of the vein shown in FIG. 7A, indicating diffuse compression without in-stent restenosis.
Figure 7A:
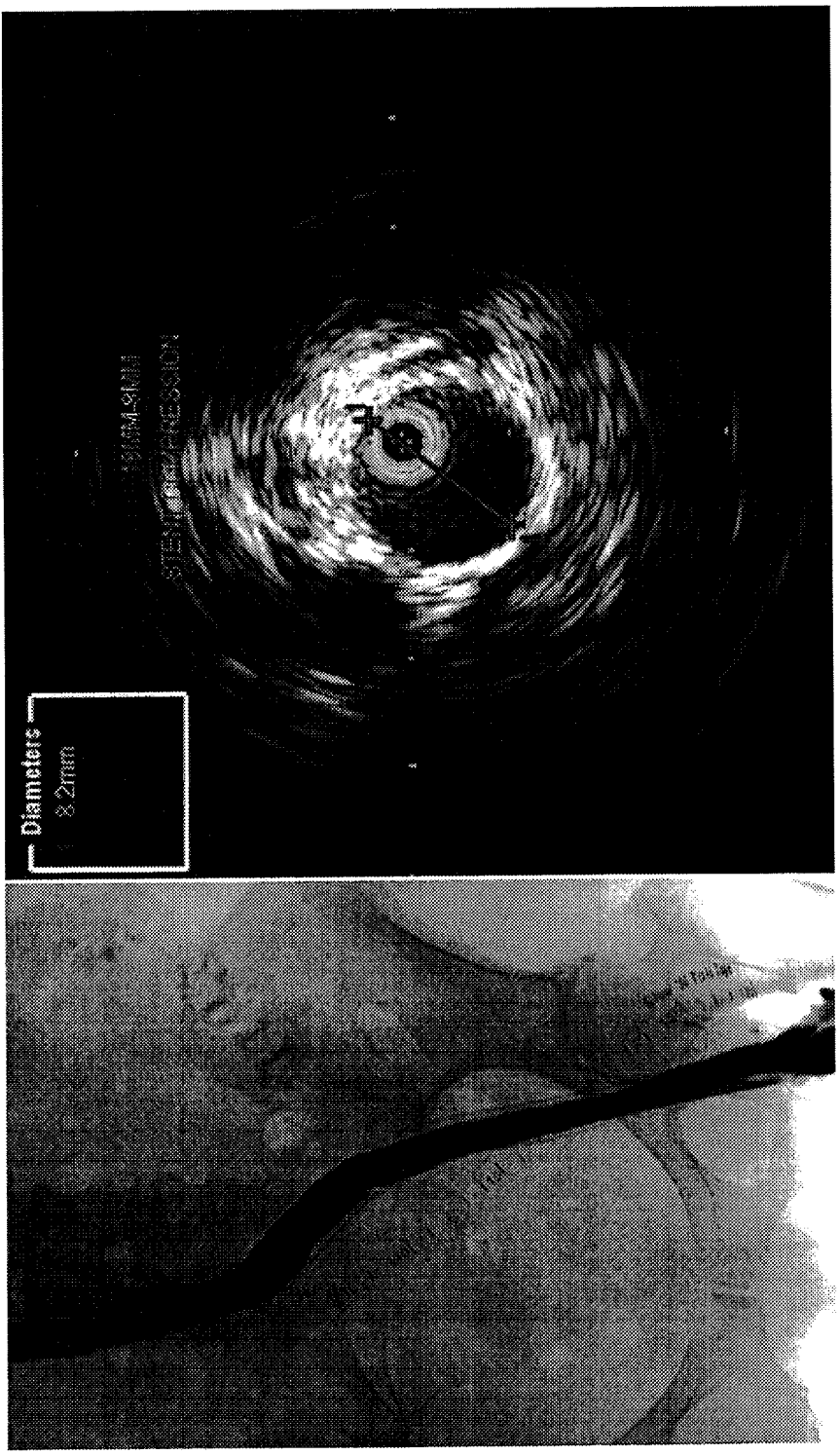
FIG. 7A is a post-intervention x-ray angiogram image of stented common and external iliac veins with no focal narrowing visible.
Figures 8A, 8B:
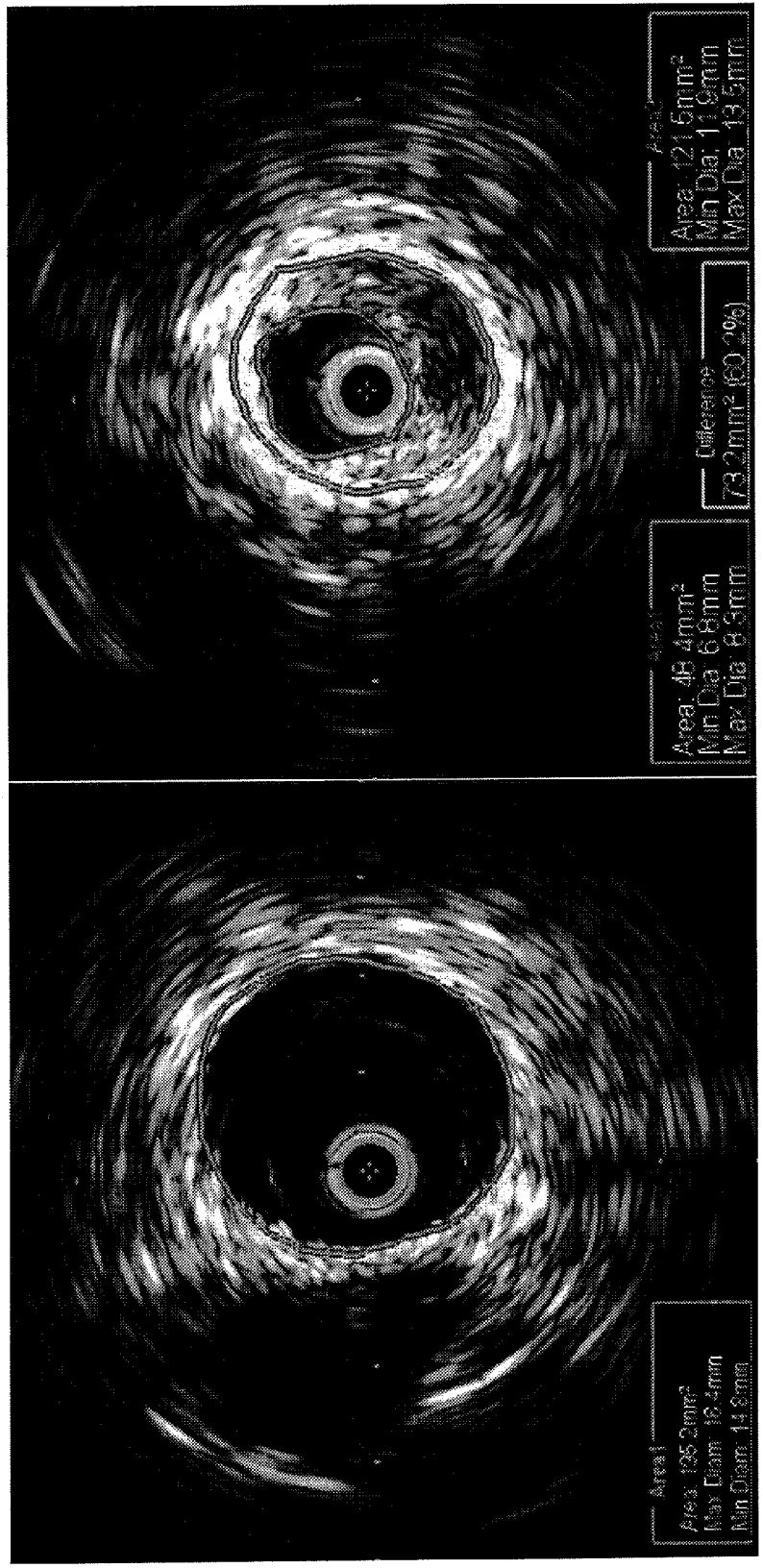
FIG. 8A is an intravascular ultrasound image of a stented common iliac vein.
FIG. 8B is an intravascular ultrasound image of the vein of FIG. 8A, taken five months later, suffering from stent compression and in-stent restenosis.

The DUS area method later described is also applicable to stent malfunction after stenting. FIG. 7A shows a venography image of a stented vein segment. FIG. 7B, is an IVUS image of the same vein and shows severe stent compression: an 18 mm wall stent was compressed down to 8 mm. Some stented areas will have combination of stent compression in-stent restenosis (stenosis occurring in the interior of a stent), or in-stent restenosis (ISR). Shown in FIG. 8A is a stented CIV vein segment immediately after stenting, having a cross-sectional area of 195 mm$^2$. Five months later, the IVUS image of FIG. 8B shows the same CIV vein segment, but with stent compression evident (the outer circular line with an area of 121.5 mm$^2$) and ISR evident (the area between the inner circular line and outer circular line. The inner cross-sectional area is 48 mm$^2$.

Figure 9B:
FIG. 9B is an intravascular ultrasound image of the stented vein of FIG. 9A after balloon dilatation.
Figure 9A:
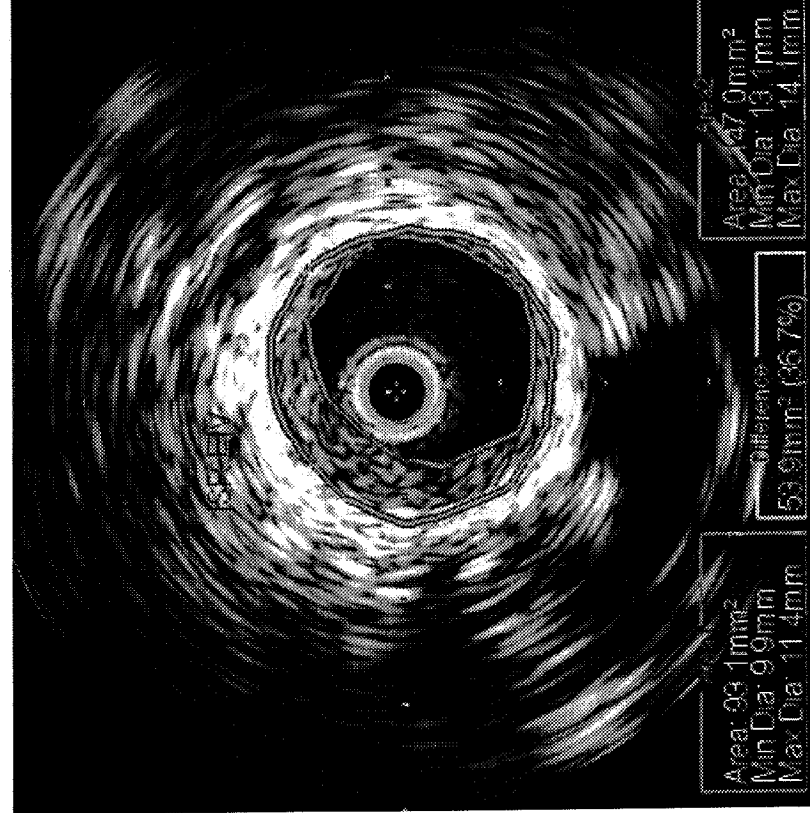
FIG. 9A is an intravascular ultrasound image of a stented external iliac vein showing in-stent restenosis.

The ISR stenosis is 60%, if calculated using the stented area of the outer diameter. This, however, will understate the stenosis, as stent compression has not been accounted for. When stent compression is taken into account, overall lumen stenosis is actually 75% (that is the cross-sectional area is 48.4 mm$^2$, reduced from the original stented area of 195.2 mm$^2$, a 75% reduction in area). Finally, FIG. 9A shows a common iliac vein segment suffering from stent compression and ISR, with a cross-sectional area of 93 mm$^2$ (>50% stenosis). After balloon dilatation, FIG. 9B shows the same vein segment's cross-sectional area of 150 mm$^2$, improved, but with mild stent compression remaining.

One embodiment is determining the vein cross-sectional area using DUS measurements, and comparing that cross-sectional area to a predetermined mean minimum cross-sectional area for the vein segment, as determined above. As the outer diameter of the vein is measured, this technique identifies stenosis occurring primarily as a result of vein compression. Instead of cross sectional measurements, a diameter measurement may be used, as the two are directly related.

Figure 10:
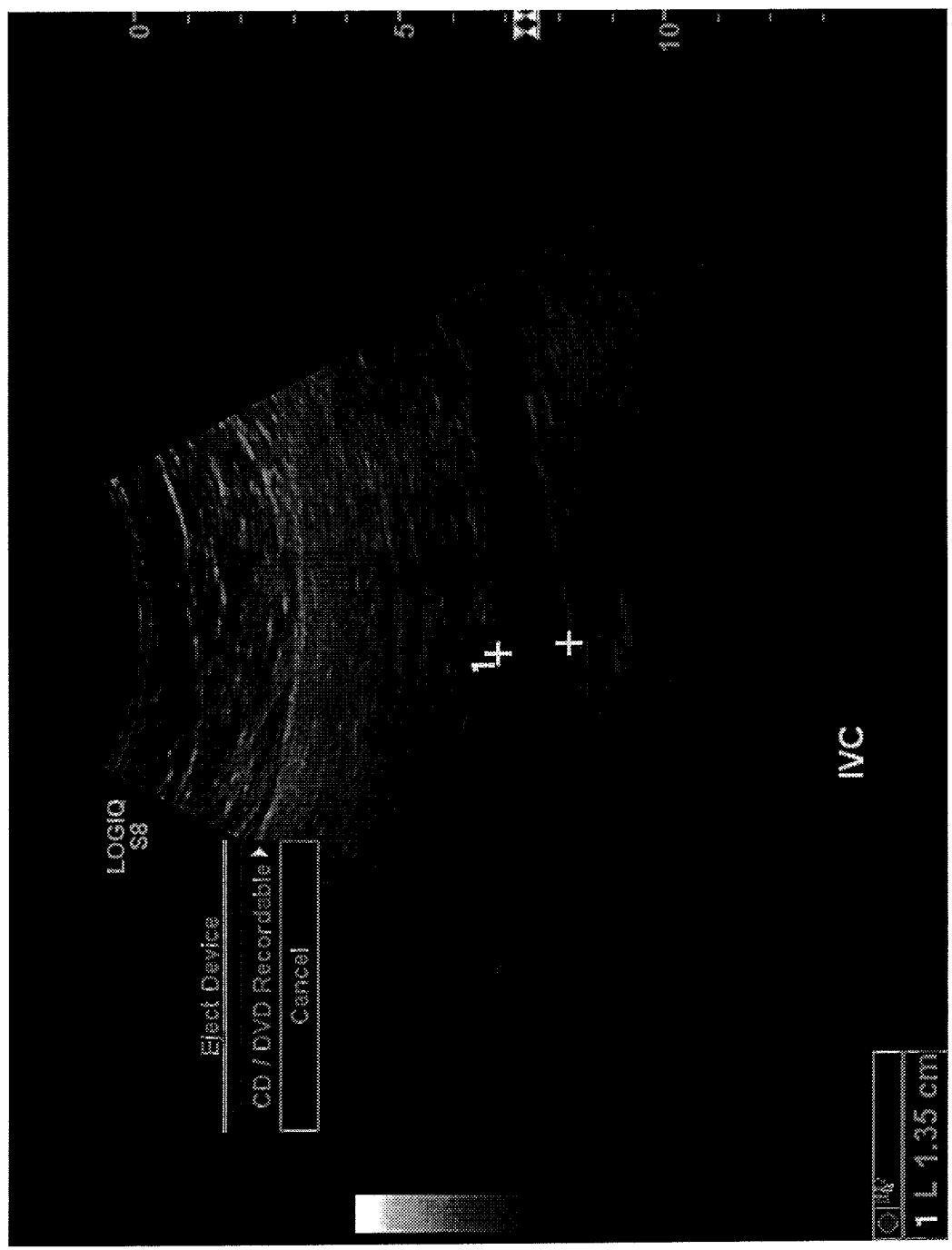
FIG. 10 is a duplex ultrasound B-Mode image of an external iliac vein showing its diameter.
Figure 11:
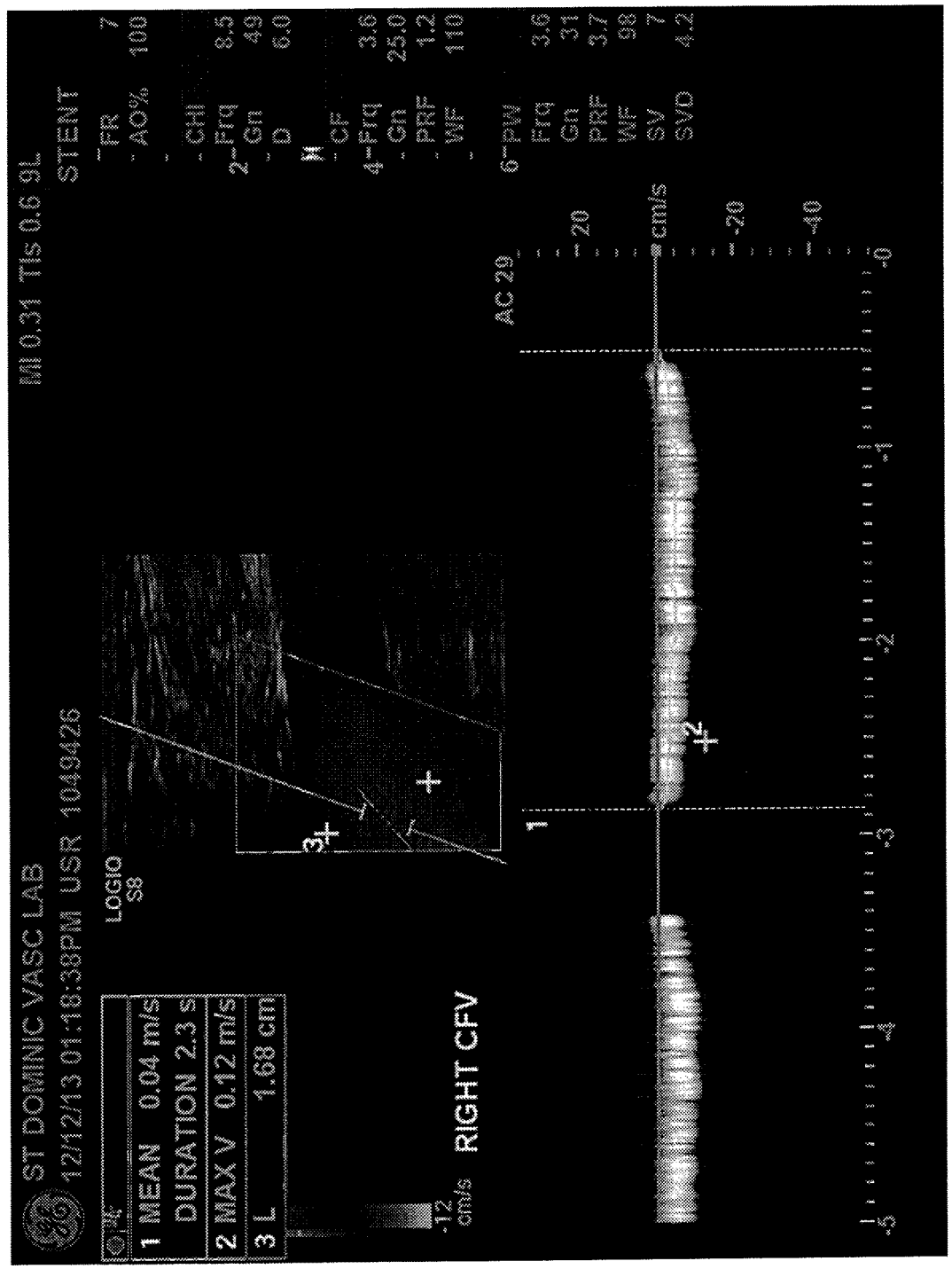
FIG. 11 is a duplex ultrasound image of the vein of FIG. 10, showing color flow rate calculated using Doppler shift techniques.

FIG. 10 shows a DUS measurement of an EIV vein, where the diameter is 13.5 mm. A cross-sectional area is calculated from the user identified vein diameter, and the DUS processor is configured to calculated the cross-sectional area, here a 140 mm$^2$ cross-sectional area. This calculated cross-sectional area is then compared to the predetermined minimum cross-sectional area as specified in Table 4, indicating a 7% stenosis. This method may be used for other veins. The interior lumen size may be measured using a color flow channel, as shown in FIG. 11, as opposed to the DUS B-mode. Calculating cross-sectional area from a DUS color view may be a convenient way to confirm that a vein is obstructed, such as by internal stenosis.

A processor may be configured to calculate a cross-sectional area based on a DUS measured vein diameter, which may be used to diagnose significant stenosis according to predetermined anatomical thresholds, identified above. The above techniques are particularly useful when diffuse stenosis is present. The techniques were verified using the following procedures.

Methods 109 unstented and 76 stented symptomatic limbs that consecutively underwent IVUS examination during the initial or re-interventional procedure respectively, were analyzed. To perform the procedure, the patient lies supine on an examination table and a gel is applied to the patients' skin in the area to be examined. The gel helps couple the transducer and transmit the sound waves. The ultrasound transducer is gently moved on the area to be examined. The transducer should be tilted up to sixty degrees from vertical, for optimal visualization of the vein to procure the parameter desired. The optimal angle may vary depending upon if the diameter or color flow rate is being imaged. As the transducer moves, the signals are transmitted to the computer that converts the reflected sound waves into images. The physician will capture a particular image of particular vein segment and store that image. For purposes of the present procedure, the image that is captured is a B-Mode or gray-scaled image that represents a two dimensional image of the vein segment, such as shown in FIG. 10. The physician will determine the narrowest point of the vein segment, and use the DUS software to "measure" the diameter of the narrowest portion.

In one particular DUS device, the physician will position electronic crosshairs on the displayed image, one crosshair on opposite sides of the vein segment of interest-cross hairs should preferably be positioned across the narrowest portion of the imaged vein segment so that the line segment between the cross hairs is near perpendicular to the vein segment walls. The DUS software will then calculate the distance (D) between the cross hairs. Some DUS devices calculate D by assigning a known distance to each pixel of the displayed image and calculating the pixel distance separating the cross hairs, and multiplying the pixel measurement by the predetermined distance represented by each pixel. The DUS software can be modified to determine the presence or absence of stenosis in the following procedure:

Calculate cross-sectional area based on the measured diameter $=(D/2)^2*\pi$.

Compare calculated area from the previous step with stored predetermined normal cross-sectional area of the vein segment, which depends on the vein segment of interest. (for instance, determine the ratio of the calculated area to the predetermined area); and display the differences. If the diameter is directly used, the comparison would be for a comparison of the measured diameter with a predetermined minimum.

If the comparison indicates the calculated cross-sectional area is less than 50% (more preferred, less than 70%, most preferred less than 90%) (if diameters are used, the ratios would be the less than √0.5, or more preferred less than √0.7, or most preferred less than √0.9 ) of the predetermined cross-sectional area as specified in Table 4, then there is an increased risk of severe stenosis; if the comparison indicates that the calculated cross-sectional area is more than the selected cutoff point, then the risk of stenosis is reduced.

Using the above procedures, the DUS determined diameter D at the narrowest point in the iliac vein or stent was used to calculate cross-sectional area ($\pi(D/2)^2$). Actual vessel cross-sectional area was measured using IVUS planimetry for comparison. If different DUS views at the same spot in the native vein or stent are taken, the largest DUS determined measured cross-sectional area should be used. This is because variations in the view angle can artificially make the area or diameter to look smaller than it is. In such instances the largest area or diameter at the same spot better represents the true diameter.

The predetermined mean cross-sectional area for the respective vein segments are: CIV=200 mm$^2$; EIV=150 mm$^2$; CFV=125 mm$^2$. Stenosis determined by traditional duplex methodology using flow measurement computed from Doppler shifts were also recorded. DUS findings (using traditional flow methods and area method) and magnetic resonance venography (MRV) findings (area method) were compared to IVUS measurements. An IVUS stenosis of≥50% of the predetermined mean cross-sectional area was used as the benchmark. Note that the area or diameter criteria denoting 'significant' stenosis is different in veins than in arteries because the former is related to venous back pressure and the latter is related to forward flow.

Figure 2:
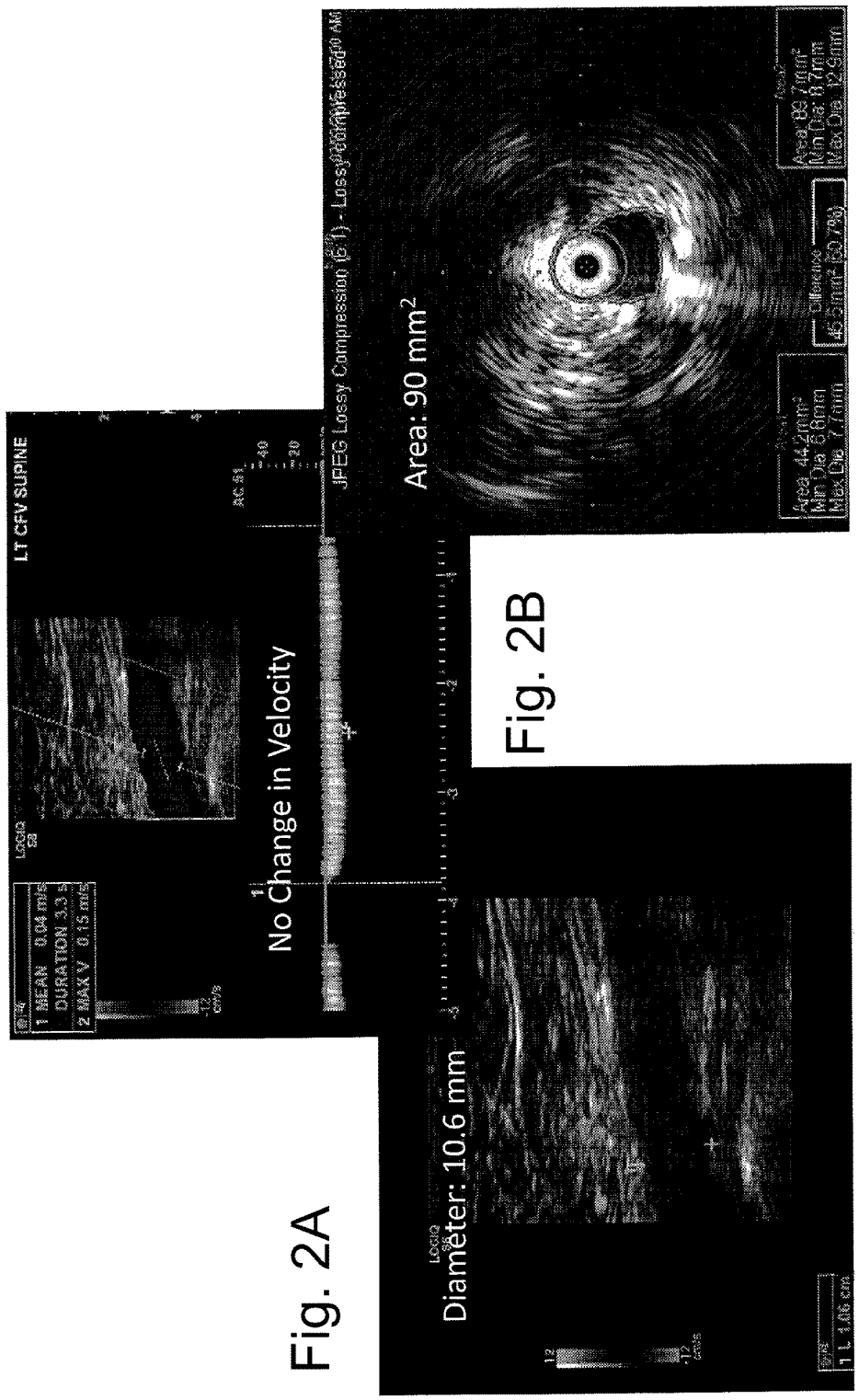
FIG. 2A is a DUS image showing a CFV vein segment diameter measurement.
FIG. 2B is a DUS Doppler measurement of fluid velocities in the vein shown in FIG. 2A.
FIG. 2C is an IVUS image of the vein shown in FIG. 2A.
Figure 12A:
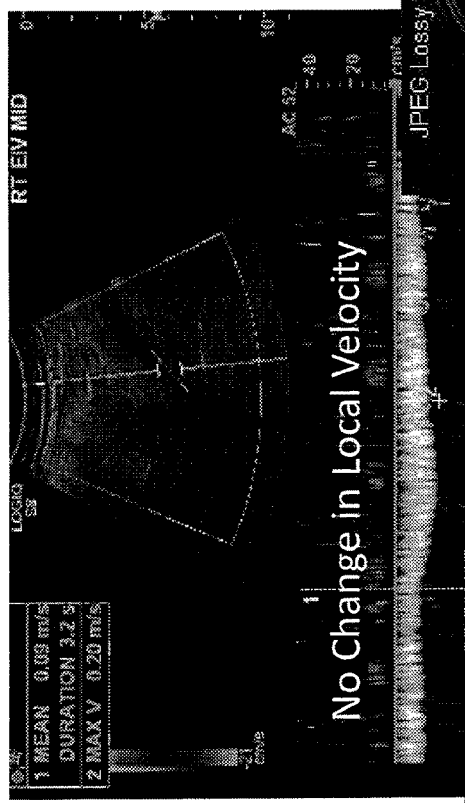
FIG. 12A is a DUS image showing a EIV vein segment diameter measurement.
Figure 12C:
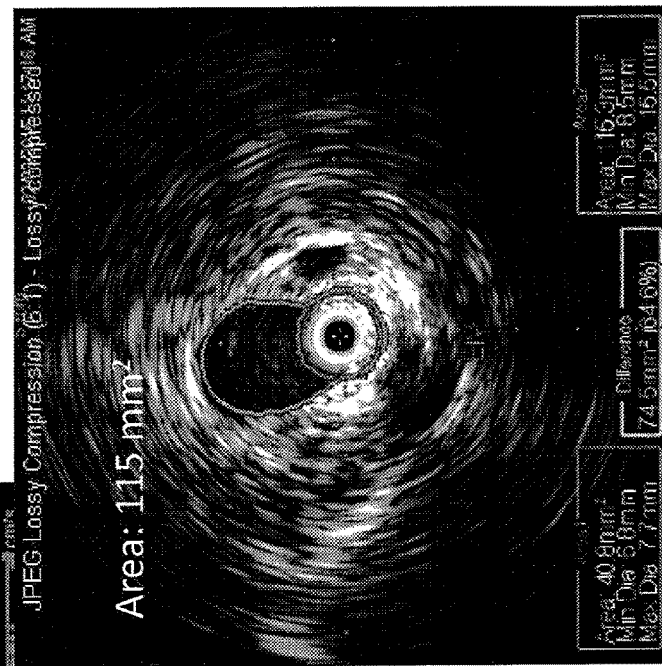
FIG. 12C is an IVUS image of the vein shown in FIG. 12A.
Figure 12B:
FIG. 12B is a DUS Doppler measurement of fluid velocities in the vein shown in FIG. 12A.
Figure 13A:
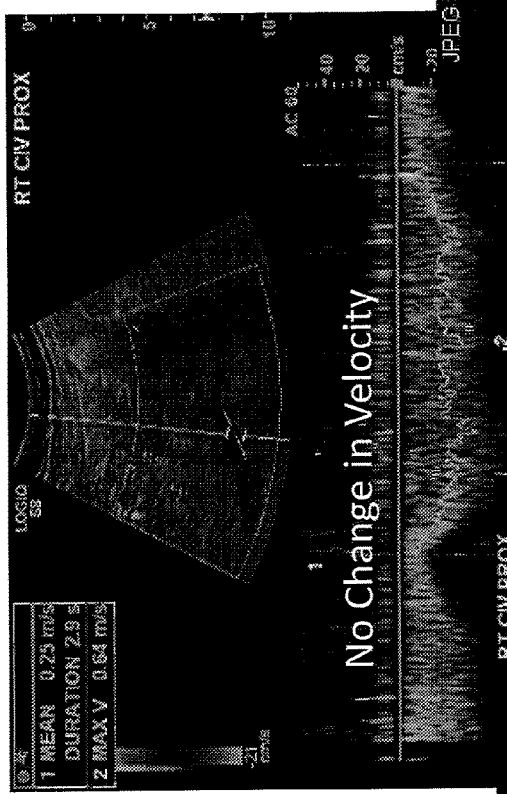
FIG. 13A is a DUS image showing a CIV vein segment diameter measurement.
Figure 13B:
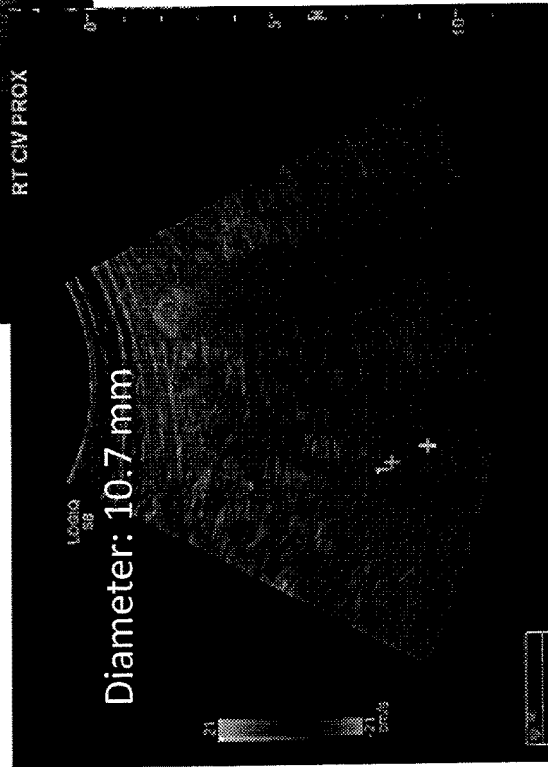
FIG. 13B is a DUS Doppler measurement of fluid velocities in the vein shown in FIG. 13A.
Figure 13C:
FIG. 13C is an IVUS image of the vein shown in FIG. 13A.

FIG. 2A is a DUS image showing a CFV vein segment diameter measurement, while FIG. 2B is a DUS Doppler measurement of fluid velocities in the vein shown in FIG. 2A. Note that the Doppler velocity measurement indicates no change in velocity in the vein segment, yet the Duplex measured diameter of 10.6 mm, using the above techniques, indicates a stenosis of about 30%. FIG. 2C is an IVUS measurement of the same vein segment, indicating a stenosis of about 28%. FIGS. 12A, B and C show similar results in a EIV vein segment (DUS indicates stenosis of about 31%, while IVUS indicates a 24% stenosis, again with no velocity change indicated by Doppler DUS measurements). FIGS. 13 A, B and C show similar results for a CIV vein segment (DUS indicates stenosis of about 55%, while IVUS indicates a 57% stenosis, again with no velocity change indicated by Doppler DUS measurements).

Variations in this procedure can include the use of more stringent cross-sectional areas for a determination of severe stenosis, for instance, such as if the DUS calculated cross-sectional area is less than 70% of the predetermined value, or less than 90% of the predetermined cross-sectional area, then the risk of severe stenosis is elevated. Obviously, instead of using cross-sectional areas, a comparison can be made between with the measured distance (D) to the predetermined mean distance or diameter (for instance, by converting the predetermined mean cross-sectional areas into predetermined mean diameter (e.g. mean diameter=2*sqrt (mean cross-sectional area/$\pi$), and modifying the variance for the predicted area accordingly.

DUS equipment continues to evolve in sophistication. 3D and 4D DUS scanners are coming on stream for vascular applications. Such instrumentation may be able to present area values directly without deriving it from a diameter (or measure the diameter directly). The direct measurement may be more accurate than deriving it from diameters derived from 2D scanners, which assumes a circular cross-section of the vein or stent lumen. An elliptical cross-section is often found on IVUS imaging. Therefore, the circular lumen assumption involves some variable degree of error. Direct area measurement with new generation 3D and 4D equipment may eliminate or minimize this error. Current patent method is inclusive of measurement improvement that may become available with newer generation DUS equipment.

The methodology also encompass using IVUS alone, bypassing a US measurement. In this case, the IVUS calculated or would again be compared with the same predetermined area that would be used for DUS comparison. With direct IVUS, if the ratio of the areas is less than 60%, more preferred, less than 50%, then stenting is indicated (note the % relates to the area unobstructed. i.e. less than 60% clear means the obstruction is greater than 40% of the minimum or optimum area). To stent, minimum stent sizes to be used should be equal to (preferably, greater, such as 2 mm greater) the minimum or optimal stent diameters shown in Table 4, for the respective vein segment.

Traditional DUS methodology, which relies on identification of focal stenosis with local velocity changes, is unreliable. Using the area method however, DUS becomes a highly sensitive tool to detect vessel stenosis/restenosis. Thus, if DUS suggests stenosis by the area method, IVUS is recommended. If DUS is negative, IVUS is likely unnecessary. Alternatively, DUS could be eliminated, and IVU alone used. Non-invasive DUS Doppler measurements and be combined with IVUS techniques to arrive at a more accurate prediction of stenosis (e.g., if velocity changes are present in a diffuse stenosis, there is an indication of internal stenosis. If velocity measurements are present in the presence of a focal stenosis, the predicted area determined stenosis can be compared with that predicted by Doppler measurements). If the Doppler predicted stenosis is higher, there is an additional indication of internal occlusion or stenosis due to buildup of deposits in the vein, in addition to that caused by local kinking or compression the vein.

TABLE 1

Normal area (Z-score > 1.65) from IVUS distribution curves of various vein segments. The respective calculated diameters are also shown as Wallstents assume a circular shape at deployment.

| Sample from distribution with a Z-score> | n | Median area (mm$^2$) | Median diameter |
|---|---|---|---|
| CIV | 16 | 220 (203- | 17 (16-19) |
| EIV | 21 | 183 (172- | 15 (15-19) |

CIV: common iliac vein;
EIV: external iliac vein.

TABLE 2

Pressure gradient in stents of different calibers at resting flow and exercise with and without 50% diameter stenosis due to ISR/compression.

| Stent diameter (mm) | Pressure (dyne/cm$^2$)[a] | | | |
|---|---|---|---|---|
| | Resting flow | Exercise flow (3×), no stenosis | 50% diameter stenosis, resting flow | 50% diameter stenosis, exercise flow (3×) |
| 8 | 302 | 907 | 4838 | 14,515 |
| 10 | 124 | 372 | 1982 | 5945 |
| 12 | 60 | 179 | 956 | 2867 |
| 14 | 32 | 97 | 516 | 1548 |
| 16 | 19 | 57 | 302 | 907 |
| 18 | 12 | 35 | 189 | 566 |
| 20 | 8 | 23 | 124 | 372 |
| | 5 | 16 | 85 | 254 |

[a]1 mmHg = 1333 dyne/cm$^2$.

TABLE 3

Diameter estimates of for the iliac-femoral vein segments derived from various methods.

| Vein Segment | From distribution curve of IVUS area in patients (n = 346) | Calculated from Poiseuille's law | Young's scaling law[b] |
|---|---|---|---|
| CIV | 17 | 18 | 19 |
| EIV | 15 | N/A | 15 |
| CFV | N/A | N/A | 12* |

[c]With a Z-score of greater than 1.65
[b]Scaling projections from IVUS data, Poiseuille calculations and Fronek's data.
*Duplex CFV diameter in a large population study by Fronek; see text CIV = common iliac vein; EIV = external iliac vein; CFV = common femoral vein; N/A: not calculated because of lack of reliable flow estimates
`Duplex CFV diameter in a large population study by Flora; see text CIV = common iliac vein; EIV = external iliac vein; CFV = common femoral vein; N/A: not calculated because of lack of reliable flow estimates.

TABLE 4

Recommended minimum stent diameter, and post-stent IVUS area for different vein segment, based on Techniques 2 and 3.

| Vessel segment | minimum Diameter | Area |
|---|---|---|
| CIV | 16-18 mm | 200-254 mm$^a$ |
| EIV | 14 mm-15 | 150 mm 176 mm$^2$ |
| CFV | 12 mm | 110 mm$^2$ or 125 mm$^2$ |

The invention claimed is:

1. A method of diagnosing and treating diffuse stenosis, comprising:
   a. Using a duplex ultrasound (DUS) to measure a cross-sectional area of a vein portion of a patient; and
   b. making a determination that the cross-sectional area is less than or equal to 90% of a calculated predetermined mean cross-sectional area fora vein segment in which the vein portion is located, where the calculated predetermined cross-sectional area is not measured from or determined from any said vein portion of said patient, or measured or determined cross sectional area of any non-stenotic vein portion in any other patient, examining the vein portion with intravascular ultrasound (IVUS) to determine an IVUS cross-sectional area of the vein portion; and
   c. making a determination that the measured IVUS cross-sectional area is less than 50% of the predetermined mean cross-sectional area for the vein segment in which the vein portion is located, treat the vein portion by stenting.

2. The method of claim 1, wherein local velocity changes as measured by DUS in the vein portion are not used to determine stenosis.

3. The method of claim 1, wherein step (c) further comprises:
   using duplex ultrasound to identify a narrowest point in the vein portion and wherein the cross-sectional area is measured at the narrowest point of the vein portion.

4. The method of claim 3, wherein a focal stenosis in the vein portion is not visually identified with DUS.

5. The method of claim 3, wherein the vein segment is chosen from a group consisting of: common iliac, external iliac, and common femoral veins.

6. The method of claim 3, wherein if the vein portion does not have a focal stenosis and the DUS measured cross-sectional area is less than or equal to 70% of the predetermined mean cross section area of the vein segment in which the vein portion is located, then diagnose the vein portion stenotic.

* * * * *